United States Patent [19]

Reiff et al.

[11] Patent Number: 5,210,273
[45] Date of Patent: May 11, 1993

[54] PROCESS FOR THE PREPARATION OF MONO- AND OLIGOURETHANES

[75] Inventors: Helmut Reiff; Dieter Dieterich, both of Leverkusen, Fed. Rep. of Germany

[73] Assignee: Bayer Aktiengesellschaft, Leverkusen, Fed. Rep. of Germany

[21] Appl. No.: 698,871

[22] Filed: May 13, 1991

Related U.S. Application Data

[63] Continuation-in-part of Ser. No. 554,037, Jul. 17, 1990, abandoned.

[30] Foreign Application Priority Data

| Jul. 25, 1989 | [DE] | Fed. Rep. of Germany ....... 3924545 |
| Jul. 9, 1990 | [CA] | Canada ................... 2020692 |
| Jul. 12, 1990 | [EP] | European Pat. Off. ......... 90113304.1 |
| Jul. 23, 1990 | [JP] | Japan ................... 2-193205 |
| Jul. 24, 1990 | [GD] | Grenada ................. 342996 |

[51] Int. Cl.$^5$ ................. C07C 269/06; C07C 229/00
[52] U.S. Cl. ..................... 560/24; 560/125; 560/127; 560/132; 560/157; 560/158; 560/162; 560/163
[58] Field of Search ............... 560/24, 125, 127, 132, 560/157, 158, 162, 163

[56] References Cited

U.S. PATENT DOCUMENTS 4,595,533  6/1986  Thompson ................. 260/239.3 R

FOREIGN PATENT DOCUMENTS 3609813  9/1987  Fed. Rep. of Germany.

OTHER PUBLICATIONS

U. Peter, Houben-Weyl, vol. E4, p. 169, 1983.
S. Julia, A. Ginebreda, Anale de Quimica, vol. 75, p. 348, 1979.

*Primary Examiner*—Jose G. Dees
*Assistant Examiner*—Porfirio Nazario
*Attorney, Agent, or Firm*—Joseph C. Gil; Richard E. L. Henderson

[57] ABSTRACT

This invention relates to a process for the preparation of N,N-disubstituted mono- and oligourethanes by the reaction of N-aromatically, N-aliphatically, N-cycloaliphatically, and N-araliphatically substituted mono- and oligourethanes with dialkyl carbonates in the presence of at least stoichiometrically equivalent quantities of solid alkali or alkaline-earth carbonate in excess dialkyl carbonate and/or an aprotic organic solvent and in the presence of a phase transfer catalyst.

12 Claims, No Drawings

PROCESS FOR THE PREPARATION OF MONO- AND OLIGOURETHANES

CROSS REFERENCE TO RELATED APPLICATION

This application is a continuation-in-part of U.S. application Ser. No. 07/554,037, filed Jul. 17, 1990, now abandoned.

BACKGROUND OF THE INVENTION

This invention relates to a process for the preparation of N,N-disubstituted mono- and oligourethanes by the reaction of N-aromatically, N-aliphatically, N-cycloaliphatically, and N-araliphatically substituted mono- and oligourethanes with dialkyl carbonates in the presence of at least stoichiometrically equivalent quantities of solid alkali or alkaline-earth carbonate (particularly potassium and/or sodium carbonate) in excess dialkyl carbonate and/or a suitable solvent and in the presence of a phase transfer catalyst.

It is known that monourethanes can be reacted with lower alkyl halides or alkyl sulfates to form N,N-disubstituted monourethanes. See U. Petersen in Houben-Weyl, Volume E4, page 169, edited by Hagemann. However, a disadvantage of the known processes is that good yields are obtained only when special, relatively expensive bases such as metal hydrides (for example, sodium hydride) are used. In addition, because the secondary reaction of olefin formation predominates under these reaction conditions when secondary alkylating agents are used, these processes are limited to the use of primary alkylating agents.

It is also known that N-aryl substituted monourethanes can be N-alkylated with alkyl halides or dialkyl sulfates under the conditions used for phase transfer catalysis. The method fails completely, however, where N-aliphatically substituted urethanes are used. See S. Julia and A. Ginebreda, *Anales de Ouimica* (Madrid), 75, 346-348 (1979) at page 348, lines 7-13.

In addition, German Offenlegungsschrift 3,609,813 describes a process for the preparation of N,N-disubstituted mono- and oligourethanes in which N-aliphatically, N-cycloaliphatically, and N-araliphatically substituted mono- and oligourethanes are reacted with alkylating agents in the presence of at least stoichiometric quantities of a solid metal hydroxide (in either the presence or absence of an aprotic organic solvent) and optionally in the presence of a phase transfer catalyst.

One common feature of all known processes is that, ultimately, the alkylations are carried out with alkylating agents, almost all of which are known to be physiologically objectionable. For example, N-alkylations are carried out with dimethyl sulfate or methyl chloride or iodide.

An object of the present invention was to provide an economic process for the alkylation of N-aromatically or N-aliphatically substituted urethanes which avoids the disadvantages described above. It has now surprisingly been found that the desired N,N-disubstituted mono- and oligourethanes can be obtained when N-aromatically, N-aliphatically, N-cycloaliphatically, and N-araliphatically substituted mono- and oligourethanes are reacted with dialkyl carbonates in the presence of at least equivalent quantities of solid alkali or alkaline earth carbonate.

SUMMARY OF THE INVENTION

The present invention relates to a process for preparing N,N-disubstituted mono- and oligourethanes comprising reacting
(a) N-aromatically, N-aliphatically, N-cycloaliphatically, and N-araliphatically substituted mono- and oligourethanes
(b) with dialkyl carbonates in the presence of
(c) at least stoichiometrically equivalent quantities of solid alkali or alkaline earth carbonates (particularly potassium and/or sodium carbonate) in excess dialkyl carbonate and/or an aprotic organic solvent and in the presence of a phase transfer catalyst.

In particular, the present invention relates to a process for preparing N,N-disubstituted mono- and oligourethanes corresponding to the general formulas

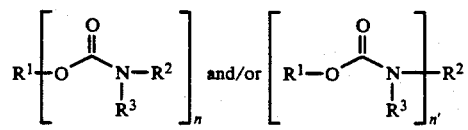

wherein
n is an integer of from 1 to 6,
n' is an integer of from 1 to 6,
$R^1$ is an n-functional aromatic, aliphatic, cycloaliphatic, or araliphatic group derived from the corresponding n-functional (i.e., monohydric to hexahydric) alcohol,
$R^2$ is an n'-functional aromatic, aliphatic, cycloaliphatic, or araliphatic group derived from the corresponding n'-functional monoisocyanate or polyisocyanate, and
$R^3$ is an aliphatic or araliphatic group derived from the corresponding dialkyl carbonate, comprising alkylating
(a) N-aromatically, N-aliphatically, N-cycloaliphatically, and N-araliphatically substituted mono- and oligourethanes corresponding to the general formulas

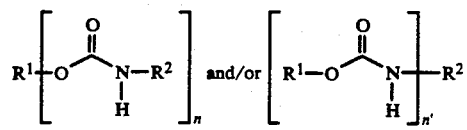

wherein n, n', $R^1$, and $R^2$ are as defined above,
(b) with dialkyl carbonates in the presence of
(c) at least stoichiometrically equivalent quantities of solid alkali or alkaline earth carbonates in excess dialkyl carbonate and/or an aprotic organic solvent and in the presence of a phase transfer catalyst.

The present invention also relates to chain-like N-alkylated oligourethanes corresponding to the general formula

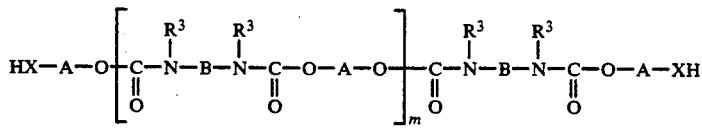

wherein
R³ is as defined above,
X is O or NH,
A is a residue of a dihydric alcohol corresponding to a difunctional R¹ group,
B is a residue of a diisocyanate corresponding to a difunctional R² group, and
m is a number of from 1 to 20,
prepared from corresponding oligourethanes containing hydrogen atoms instead of R³ groups.

DETAILED DESCRIPTION OF THE INVENTION

To obtain good yields using the process of the invention, it is particularly advantageous to dissolve the starting urethane, the dialkyl carbonate, and the phase transfer catalyst in an aprotic organic solvent (preferably dimethyl sulfoxide, chlorobenzene, dimethylformamide, or N-methylpyrrolidone) or in an excess of the dialkyl carbonate, and then to add the dry, powdered alkali or alkaline earth carbonate (preferably potassium carbonate and/or sodium carbonate) and stirring the mixture at 90° to 140° C. until the reaction is complete.

Compared to the known processes, the process of the invention allows the surprisingly easy preparation of N,N-disubstituted urethanes in high yields by using inexpensive, less dangerous, and easily handled substances, such as alkali or alkaline earth carbonates and dimethyl carbonate, instead of the more dangerous metal hydrides and alkylating agents.

It is particularly surprising that, in contrast to the processes described in the literature, even N-aliphatically substituted urethanes can be alkylated by the process according to the invention, although longer reaction times are involved.

The N-alkylated products formed according to the present invention by transfer of the R³ group should, of course, be distinguished from N-acylated products formed by reaction of dialkyl carbonates with basic amine nitrogen atoms. E.g., U.S. Pat. No. 4,595,533.

Suitable starting materials for the process according to the invention include urethanes that may be prepared, for example, by reaction using known methods of aromatic, araliphatic, aliphatic, or cycloaliphatic mono- and oligoisocyanates with monohydric to hexahydric alcohols in the melt or in solution and optionally in the presence of a catalyst. These urethanes, however, may also be prepared, for example, by condensation of primary mono- or oligoamines with chloroformic acid esters of monohydric to hexahydric alcohols or by reaction of carbamic acid chlorides with alcohols.

Alcohols which may be used for the preparation of the urethanes used as starting materials for the process of the invention include n-functional alcohols corresponding to the formula
R¹(OH)$_n$ wherein
n is an integer of 1 to 6 (preferably 1 to 4) and
R¹ is an n-functional aromatic hydrocarbon group containing 6 to about 18 (preferably 6 to 13) carbon atoms, an aliphatic hydrocarbon group containing 1 to about 18 (preferably 1 to 6) carbon atoms, a cycloaliphatic hydrocarbon group containing 4 to about 30 (preferably 6 to 15) carbon atoms, or an araliphatic hydrocarbon group containing 7 to about 30 (preferably 7 to 15) carbon atoms.

Suitable alcohols include monohydric alcohols of the type described, for example, in Ullmanns *Enzyklopädie der Technischen Chemie*, Volume 7, 4th Edition (1974), pages 205 to 206, as well as phenols and substituted phenols.

Suitable polyhydric alcohols include ethylene glycol, 1,2- and 1,3-propylene glycol, 1,4- and 2,3-butylene glycol, 1,6-hexanediol, 1,8-octanediol, neopentyl glycol, 1,4-bis(hydroxymethyl)cyclohexane, 2-methyl-1,3-propanediol, glycerol, trimethylolpropane, 1,2,6-hexanetriol, 1,2,4-butanetriol, trimethylolethane, pentaerythritol, quinitol, mannitol and sorbitol, formitol, methyl glycoside, and/or 1,4-, 3,6-dianhydrohexatols, as well as polyhydric phenols, such as pyrocatechol, resorcinol, hydroquinone, and polynuclear phenols, such as the bisphenol A type. Mixtures of these alcohols may, of course, also be used.

Isocyanates which can be use for the preparation of the urethanes used as starting materials for the process of the invention include n'-functional isocyanates corresponding to the general formula R²(NCO)$_{n'}$ wherein
n' is an integer of from 1 to 6 (preferably from 1 to 3) and
R² is an n'-functional aromatic, araliphatic, cycloaliphatic, or aliphatic hydrocarbon group containing from 1 to 28 (preferably from 2 to 18) carbon atoms.

Suitable isocyanates include methane, ethane, propane, butane, pentane and hexane isocyanate; 6-chlorohexyl isocyanate; cyclohexane isocyanate; benzyl isocyanate; tetramethylene diisocyanate; hexamethylene diisocyanate; decamethylene diisocyanate; 1,3-di(3-isocyanatopropoxy)-2,2-dimethylpropane; cyclohexane-1,4-diisocyanate; methyl cyclohexane-2,4-diisocyanate, methyl cyclohexane-2,6-diisocyanate, and mixtures thereof; 1,3-diisocyanatocyclohexane; dicyclohexylmethane-4,4'-diisocyanate; 1-isocyanato-3-isocyanatomethyl-3,5,5-trimethylcyclohexane (isophorone diisocyanate; see German Auslegeschrift 1,202,785 and U.S. Pat. No. 3,401,190); 1,2-di(isocyanatomethyl)-cyclobutane; m- and p-xylylene diisocyanate; and α,α,α',α'-tetramethyl-m- and/or -p-xylylene diisocyanate; or -hexahydroxylylene diisocyanate. Other preferred isocyanates are phenyl isocyanate, the isomeric tolyl isocyanates, 3-chlorophenyl isocyanate, 4-chlorophenyl isocyanate, 3,4-dichlorophenyl isocyanate, the isomeric nitrophenyl isocyanates, the isomeric naphthyl isocyanates, and the like.

More generally, suitable polyisocyanate starting components include aliphatic, cycloaliphatic, araliphatic, aromatic and heterocyclic polyisocyanates such as those described, for example, by W. Siefken in *Justus Liebios Annalen der Chemie.* 562, pages 75-136. Examples of suitable polyisocyanates include, in addition to those described above, ethylene diisocyanate, 1,4-tetramethylene diisocyanate, 1,12-dodecane diisocyanate, cyclobutane-1,3-diisocyanate, 2,4- and 2,6-hexahydrotoluene diisocyanate and mixtures of these isomers, hexahydro-1,3- and/or 4,4-phenylene diisocyanate, perhydro-2,4'- and/or -4,4'-diphenylmethane diisocyanate, 1,3- and 1,4-phenylene diisocyanate, 2,4- and 2,6-tolylene diisocyanate and mixtures of these isomers, diphenylmethane-2,4'- and/or -4,4'-diisocyanate, naphthylene-1,5-diisocyanate, triphenylmethane-4,4',4''-triisocyanate, polyphenyl polymethylene polyisocyanates of the type obtained by condensing aniline with formaldehyde followed by phosgenation such as described in British Patents 874,430 and 848,671, m- and p-isocyanatophenylsulfonyl isocyanates according to U.S. Pat. No. 3,454,606, perchlorinated aryl polyisocyanates such as described in German Auslegeschrift 1,157,601 (U.S. Pat. No. 3,277,138), polyisocyanates containing carbodiimide groups such as described in German Patentschrift 1,092,007 (U.S. Pat. No. 3,152,162), diisocyanates such as described in U.S. Pat. No. 3,492,330, polyisocyanates containing allophanate groups such as described in British Patent 994,890, Belgian Patent 761,626 and published Dutch Patent Application 7,102,524, polyisocyanates containing isocyanurate groups such as described in U.S. Pat. No. 3,001,973, German Patentschriften 1,022,789, 1,222,067, and 1,027,394, German Offenlegungsschriften 1,929,034 and 2,004,048, polyisocyanates containing urethane groups such as described in Belgian Patent 752,261 or U.S. Pat. No. 3,394,164, polyisocyanates containing acylated urea groups according to German Patentschrift 1,230,778, polyisocyanates containing biuret groups such as described in German Patentschrift 1,101,394 (U.S. Pat. Nos. 3,124,605 and 3,201,372) and British Patent 889,050, polyisocyanates produced by telomerization reactions such as described in U.S. Pat. No. 3,654,106, polyisocyanates containing ester such as described in British Patents 965,474 and 1,072,956, U.S. Pat. No. 3,567,763, and in German Patentschrift 1,231,688, reaction products of the above-mentioned diisocyanates with acetals according to German Patentschrift 1,072,385, and polyisocyanates containing polymeric fatty acid esters according to U.S. Pat. No. 3,455,883.

It is also possible to use the isocyanate-group-containing distillation residues obtained in the commercial production of isocyanates, optionally in solution in one or more of the above-mentioned polyisocyanates. It is also possible to use any mixtures of the polyisocyanates described above.

In general, it is particularly preferred to use the commercially readily available polyisocyanates, for example, 2,4- and 2,6-tolylene diisocyanate, as well as any mixtures of these isomers ("TDI"), polyphenyl polymethylene polyisocyanates of the type obtained by condensing aniline with formaldehyde, followed by phosgenation ("crude MDI"), and polyisocyanates containing carbodiimide groups, urethane groups, allophanate groups, isocyanate groups, urea groups, or biuret groups ("modified polyisocyanates").

For cycloaliphatic diisocyanates, stereoisomers or mixtures thereof can be used.

Mixtures of the isocyanates described above can, of course, also be used.

Suitable dialkyl carbonates for the process of invention include compounds corresponding to the formula

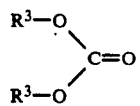

wherein $R^3$ is an aliphatic or araliphatic hydrocarbon group containing 1 to 18 (preferably 1 to 10) carbon atoms. As used herein, the term "aliphatic" refers to straight or branched chain aliphatic hydrocarbon groups, including optionally unsaturated aliphatic hydrocarbon groups, and the term "araliphatic" refers to aliphatic groups bearing with optionally substituted aromatic hydrocarbon substituents. Hence, the term "dialkyl carbonate" can refer to carbonate diesters of the above formula in which $R^3$ is an aliphatic or araliphatic group. The hydrocarbon group $R^3$ may, of course, also contain other functional groups provided they are inert under the reaction conditions according to the invention or react in a definite way with the reagents according to the invention. Suitable such functional groups include nitro, certain ester, urethane amide, and sulfonyl groups, nonlabile aromatically bound halogen, epoxide groups, aziridine groups, ether groups, thioether groups, and the like. Examples of suitable dialkyl carbonates include dimethyl carbonate, diethyl carbonate, dipropyl carbonate, dibutyl carbonate, dipentyl carbonate, and the like. Diallyl carbonate, divinyl Carbonate, optionally substituted dibenzyl carbonates, bis(nitrophenyl) carbonates, and the like are also suitable. Mixtures of these carbonates may of course also be used. Particularly preferred dialkyl carbonates are dimethyl carbonate and diethyl carbonate.

The process according to the invention may be carried out either in an aprotic organic solvent or in an excess of liquid dialkyl carbonate in the presence of a phase transfer catalyst.

Solid, finely powdered alkali metal or alkaline earth metal carbonates, such as potassium and sodium carbonate, are used as bases in the process of the invention. Potassium carbonate is preferred. Lithium, calcium, magnesium, and barium carbonates may, of course, also be used, either alone or as part of a mixture of metal carbonates. It can often be advantageous to use mixtures of these carbonates.

Phase transfer catalysts are also used in the process of the invention. Phase transfer catalysts are described, for example, in E.V. and S.S. Dehmlow, *Phase Transfer Catalysis,* 2nd Edition, Verlag Chemie (1983). Suitable phase transfer catalysts include quaternary ammonium or phosphonium salts corresponding to the formula

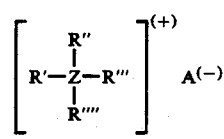

wherein
Z represents nitrogen or phosphorus,
R', R'', R''' and R'''' may be the same or different and represent $C_1$-$C_{18}$ alkyl groups, although one of these substituents may be a $C_7$-$C_{15}$ araliphatic group, wherein the sum of the carbon atoms in the four substituents is preferably from 12 to 29, and A is a monofunctional anion, such as fluoride, chloride, bromide, iodide, hydrogen sulfate, or a phosphonate.

Typical examples of suitable phase transfer catalysts include N-benzyl-N,N,N-triethylammonium chloride or bromide, N-benzyl-N-dodecyl-N,N-dimethylammonium chloride or bromide, N,N,N,N-tetrahexylammonium chloride or bromide, N-benzyl-N,N,N-trioctylammonium chloride or bromide, or the phosphonium salts corresponding to these ammonium salts. Other phase transfer catalysts according to the invention include tetrabutylammonium bromide, tetrabutylammonium iodide, tetrabutylammonium bromide plus dimethylformamide, tetrabutylammonium chloride, tetrabutylammonium hydrogen sulfate, 1:1 tetrabutylammonium bromide/sodium iodide, tetraethylammonium chloride, zephirol saccharinate, tricaproylmethylammonium chloride, crown ether 18, benzyltrimethylammonium fluoride, cetyltrimethylammonium bromide, tetrabutylphosphonium bromide, benzyltrimethylammonium chloride. Preferred phase transfer catalysts include tetrabutylammonium chloride, tetrabutylammonium bromide, tetrabutylammonium iodide, benzyltriethylammonium chloride and bromide, and benzyltrimethylammonium chloride and bromide.

The starting urethanes described above may be reacted with the dialkyl carbonate in a stoichiometric quantity, in excess, or in a substoichiometric quantity (based on the number of urethane groups present in the molecule). A ratio of 0.9–15 mole of dialkyl carbonate per mole of urethane groups is preferred, with a ratio of 1 to 5 mole of dialkyl carbonate per mole of urethane groups being particularly preferred. When a substoichiometric quantity of dialkyl carbonate is used, only partial alkylation is, of course, achieved. The use of a relatively large excess need not be uneconomical, however, because the excess can be recycled.

The reaction is generally carried out continuously or discontinuously at reduced of pressure at a temperature in the range of about 20 to about 180° C. (preferably from 80° to 140° C.).

It is particularly preferred to carry out the reaction in excess dialkyl carbonate or in a polar aprotic organic solvent. Suitable aprotic organic solvents are those which are inert under the reaction conditions according to the invention, such as those described in Ullmanns *Enzyklopadie der Technischen Chemie*, Volume 14, 4.E-dition, (Verlag Chemie 1978), page 305. Suitable solvents include benzene, toluene, xylene, ethylbenzene, cumene, methylene chloride, chloroform, dichlorobenzene, trichlorobenzene, nitrobenzene, acetone, methyl ethyl ketone, diethyl ketone, cyclohexanone, diethyl ether, diisopropyl ether, tetrahydrofuran, dioxane, dimethylformamide, dimethylacetamide, dimethyl sulfoxide, tetramethylene sulfone, furfurol, nitromethane, nitroethane, nitropropane, N-methylpyrrolidone, and hexamethylene phosphoric acid triamide. Dimethyl sulfoxide, chlorobenzene, dimethylformamide, N-methylpyrrolidone, and tetramethylene sulfone are preferred. Mixtures of these solvents may, of course, also be used.

In the practical application of the process according to the invention, the quaternary ammonium or phosphonium salts are preferably used in bulk and preferably in a quantity of from 1 to 10 mole-percent, based on the number of moles of urethane groups present.

The process according to the invention may be carried out, for example, by initially introducing the urethane, the dialkyl carbonate, and the phase transfer catalyst in the selected solvent and then adding with stirring the dry, very finely ground solid alkali carbonate all at once, in portions, or continuously. The reaction mixture is then stirred at elevated temperature, for example at 80 to 140.C, until analysis by thin-layer chromatography or gas chromatography indicates complete conversion.

The reaction mixture may be worked up by known methods. Where the solvents are water miscible and the reaction products are water-insoluble solids, the reaction mixture may be stirred into water and the precipitated reaction product may be isolated by suction filtration in the usual manner. On the other hand, oily reaction products are best worked up by standard extraction methods. If necessary, the crude products may be purified by conventional methods such as recrystallization or distillation.

The N,N-disubstituted urethanes obtainable by the process of the invention are active ingredients and valuable starting materials for the production of dyes, pharmaceutical products, and heat-stable synthetic materials. The N,N-disubstituted urethanes of the invention show higher thermal, thermooxidative, and photooxidative stability (see R. Vieweg, A Hochtlen, Kunststoff Handbuch, Volume VII, Polyurethane (Hanser Verlag, Munich 1966), pages 11 and 21) and more favorable burning behavior than the corresponding N-monosubstituted urethanes.

It is possible to hydrolyze the N,N-disubstituted urethanes to prepare the corresponding substituted secondary amines, which are also important starting materials for the synthesis of active ingredients and for the preparation and formulation of plastics.

All of the reaction products were analyzed for purity by gas chromatography or thin layer chromatography and their identities were established by IR and NMR spectra. In addition, the reaction can be conveniently monitored by IR spectroscopy because bands characteristic of N-monosubstituted urethanes at 3200–3500 cm$^{-1}$ (N-H stretch) and 1530–1560 cm$^{-1}$ (N-H bend) disappear in the course of the reaction.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1 Preparation of N-methyl-N-phenyl-O-methyl urethane (or methyl N-methyl-N-phenylcarbamate)

Methyl N-phenylcarbamate (15.1 g, 0.1 mole) was initially mixed in a reactor together with 100 ml of dimethyl carbonate. Ground and dried potassium carbonate (5 g, 0.036 mole) and tetrabutylammonium bromide (1 g, 0.003 mole) were successively added with stirring at room temperature. After heating to the reflux temperature (95°–97° C.), the reaction mixture was stirred for 7 days at that temperature.

The solution was then hot-filtered, cooled, and freed from the solvent in a rotary evaporator. The resultant clear light brown oil (14.8 g) was distilled in a bulb tube furnace (Buchi model GKR-50) at approximately 150° C. at 0.01 mbar, yielding 13 g (88% of the theoretical) of the desired product having the formula:

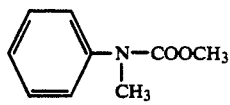

Example 2

The procedure was exactly the same as in Example 1, varied to illustrate the diversity of the products. Cosolvent (if any), secondary products (if any), and/or unreacted starting material (if any) are listed under "Remarks".

The phase transfer catalysts used are abbreviated as follows:

| TBAB | tetrabutylammonium bromide |
|------|---------------------------|
| BTMAC | benzyltrimethylammonium chloride |
| TBAI | tetrabutylammonium iodide |
| CTMAB | cetyltrimethylammonium bromide |

TABLE 1
Alkylation of Urethanes with Dimethyl Carbonate

| Example | Starting Material | Catalyst | Main Product | Yield | Days | Remarks |
|---------|-------------------|----------|--------------|-------|------|---------|
| 4 | Ph-N(H)-C(O)-OCH$_3$ | TBAB | Ph-N(CH$_3$)-C(O)-OCH$_3$ | 93% | 1 | Tetramethylene sulfone |
| 5 | | BTMAC | | 78% | 14 | — |
| 6 | Ph-N(H)-C(O)-O-C$_2$H$_5$ | BTMAC | Ph-N(CH$_3$)-C(O)-OR | 82% | 14 | R = CH$_3$ and C$_2$H$_5$ (45:55) |
| 7 | O$_2$N-C$_6$H$_4$-N(H)-C(O)-OCH$_3$ | TBAB | O$_2$N-C$_6$H$_4$-N(CH$_3$)-CO-CH$_3$ | 54% | 1 | — |
| 8 | Tolylene diisocyanate bis(methyl urethane) | BTMAC | CH$_3$-C$_6$H$_3$[N(CH$_3$)C(O)OCH$_3$][N(CH$_3$)C(O)CH$_3$] | 68 | 11 | Also monoalkyl |
| 9 | Same as Ex. 8 | TBAB | | 90 | 5 | — |
| 10 | CH$_3$(CH$_2$)$_3$-N(H)-C(O)-OCH$_3$ | BTMAC | CH$_3$(CH$_2$)$_3$-N(CH$_3$)-C(O)-OCH$_3$ | 39 | 11 | Tetramethylene sulfone; starting product |
| 11 | Hexamethylene diisocyanate bis(methyl urethane) | TBAB | CH$_3$OC(O)-N(CH$_3$)-(CH$_2$)$_6$-N(CH$_3$)-C(O)-OCH$_3$ | 10 | 5 | Monoalkyl |
| 12 | Same as Ex. 11 | TBAB | Same as Ex. 11 | 74 | 18 | DMSO; monoalkyl |
| 13 | Same as Ex. 11 | TBAI | Same as Ex. 11 | 63 | 14 | N-methylpyrrolidone |
| 14 | Same as Ex. 11 | CTMAB | Same as Ex. 11 | 60 | 14 | N-methylpyrrolidone | except that the reaction was carried out in the presence of 100 ml of N-methylpyrrolidone ("NMP"). After two days at reflux, no more starting product could be detected by gas chromatography. The yield was 99% of the theoretical of N-methyl-N-phenyl-O-methyl urethane.

Example 3

The procedure was exactly the same as in Example 1, except that 100 ml of dimethyl sulfoxide ("DMSO") were used. The product was obtained in a yield of 96% of the theoretical.

Examples 2 and 3 show a distinct acceleration of the reaction by polar aprotic solvents.

Examples 4–14

Examples 4–14 are summarized in Table 1. In all the reactions, dimethyl carbonate was used in exactly the same way as in Example 1. The starting urethanes were

Example 15  Bis(N-methyl)-2,4-TDI-bis(methyl urethane) (or 2,4-bis[N-methyl(methoxycarbamido)]toluene)

Dried and ground potassium carbonate (10 g, 0.072 mole) and benzyltrimethylammonium chloride (2 g, 0.01 mole) were added at room temperature to 2,4-toluene diisocyanate bis(methyl urethane) (23.8 g, 0.1 mole) in 200 ml of dimethyl carbonate. After stirring under reflux for 15 days (94°–97° C.), no residual starting material was detected. The reaction mixture was cooled, the insoluble component was filtered off, and the mother liquor was concentrated in a rotary evaporator. The resultant oil was distilled at 200° C./0.01 mbar in a bulb tube furnace, giving 14.7 g of the desired end product (80% of the theoretical) having the formula

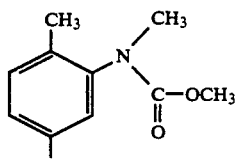

Examples 16–25

Table 2 summarizes reactions carried out in accordance with the invention using other dialkyl carbonates. Within this group, diethyl carbonate is particularly suitable.

TABLE 2

Alkylation of Urethane (Cat.: TBAB)

| Example | Starting Material | Reagent | Main product | Days | Yield | Remarks |
|---|---|---|---|---|---|---|
| 16 | Ph-NH-COOC₂H₅ | DEC | Ph-N(C₂H₅)-COOC₂H₅ | 5 | 51% | — |
| 17 | | | | 3 | 83% | DMSO |
| 18 | | | | 2 | 81% | NMP |
| 19 | Ph-NH-COO-allyl | ALLC | Ph-N(allyl)-COO-allyl | 3 | 20% | — |
| 20 | | | | 4 | 35% | DMSO |
| 21 | Ph-NH-COOC₂H₅ | ALLC | Ph-N(allyl)-COO-allyl | 7 | 44% | Ph-N(allyl)-COO-C₂H₅ (33%) |
| 22 | | | | 3 | 87% | NMP |
| 23 | Ph-NH-COO-benzyl | BENC | Ph-N(benzyl)-COO-benzyl | 4 | 81% | — |
| 24 | | | | 2 | 20% | DMSO |
| 25 | | | | 4 | 89% | NMP |

DEC—Diethyl carbonate
ALLC—Diallyl carbonate
BENC—Dibenzyl carbonate in addition to 10% of a monobenzylated product corresponding to the formula

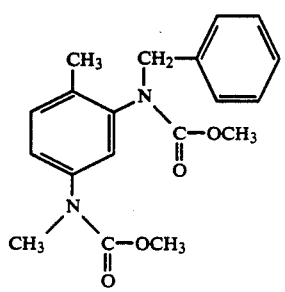

Examples 26 to 31

The following Examples illustrate the diversity of the alkali and alkaline earth carbonates suitable for the process according to the invention.

Basic Mixture

| | |
|---|---|
| 10 g | N-phenyl-O-methyl urethane |
| 150 g | dimethyl carbonate |
| 1 g | tetrabutylammonium bromide |
| 5 g | base as in Example 1 |

TABLE 3

Yields (%) of N-phenyl-N-methyl-O-methyl urethane

| | Example | | | | | |
|---|---|---|---|---|---|---|
| Base | 26 Na₂CO₃ | 27 K₂CO₃ | 28 K₂CO₃ pyridine (1:1) | 29 CaCO₃ | 30 MgCO₃ | 31 MgO.MgCO₃ |
| Yield (2 days/95° C.) | 99.0 | 96.5 | 98.2 | 99.5 | 98.6 | 68.2 |
| Yield (3 days/95° C.) | * | * | 99.3 | * | * | 88.8 |

*Reaction terminated after 2 days

Example 32 a. Preparation of an OH-terminated oligourethane 2,4-Tolylene diisocyanate (261 g, 1.5 mole) was added dropwise with stirring at 50°–70° C. to neopentyl glycol (208 g, 2.0 mole) in 203 g of anhydrous dimethyl sulfoxide. After the temperature was increased to 80° C., the reaction mixture was stirred for approximately 2 hours until no more isocyanate groups could be detected by IR spectroscopy. A 70% solution of an OH-terminated oligourethane in dimethyl sulfoxide was obtained (theoretical molecular weight of 940).

b. Preparation of the homologous N-methyl product according to the invention

Dimethyl carbonate (700 ml), tetrabutyl ammonium bromide (3 g), and potassium carbonate (25 g) were added to the above mixture (Example 32a), followed by stirring for 4 days at an internal temperature of 95.C. After cooling, filtration under suction, and removal of the solvent, a viscous pale yellow non-crystallizing resin was obtained in a 99% yield.

To remove catalyst residues, a sample of this material was distributed between water and methylene chloride and the methylene chloride phase was washed with water, dried, and freed from the methylene chloride. The degree of alkylation as determined by proton NMR was 93.6%.

Example 33 a. Preparation of an OH-terminated oligourethane 2,4-Tolylene diisocyanate (145 g, 0.833 mole) was added dropwise at 60 C. to a solution of 2,5-hexanediol (146 g, 1.237 mole) in 200 ml of dimethyl carbonate and the mixture was stirred at 90° C. until isocyanate could no longer be detected by IR spectroscopy. A 58.45% solution in dimethyl carbonate of an OH-terminated oligourethane having a calculated molecular weight of 1745 was obtained in a quantitative yield. The product was a crystallizing resin.

b. Preparation of the homologous N-methyl product according to the invention

The above solution (Example 33a) was diluted with another 300 ml of dimethyl carbonate and potassium carbonate (30 g) and tetrabutylammonium bromide (3 g) were added. The mixture was stirred for 9 days at 95° C. After cooling, the potassium carbonate was filtered off, the organic solution was washed twice with 150 ml water, and the solvent was distilled off. The degree of alkylation of the end product as determined by proton NMR was 97.3% of the theoretical. A viscous non-crystallizing light-colored resin was obtained in a yield of 95% of the theoretical.

What is claimed is:

1. A process for preparing an N,N-disubstituted mono- or oligourethane comprising reacting
   (a) an n-aromatically, n-aliphatically, N-cycloaliphatically, or n-araliphatically substituted mono- or oligourethane
   (b) with a dialkyl carbonate in the presence of
   (c) at least stoichiometrically equivalent quantities of a solid alkali or alkaline earth carbonate in excess dialkyl carbonate, an aprotic organic solvent, or a mixture thereof, and in the presence of a phase transfer catalyst.

2. A process according to claim 1 wherein component (a) is one or more members selected from the group consisting of
   (i) an n-aromatically, n-aliphatically, N-cycloaliphatically, or N-araliphatically substituted mono- or oligourethane corresponding to the formula

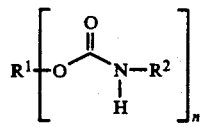

wherein
n is an integer of from 1 to 6,
$R^1$ is an n-functional aromatic hydrocarbon group containing 6 to 18 carbon atoms, aliphatic hydrocarbon group containing 1 to 18 carbon atoms, cycloaliphatic hydrocarbon group containing 4 to 30 carbon atoms, or araliphatic hydrocarbon group containing 7 to 30 carbon atoms, and
$R^2$ is an monofunctional aromatic, araliphatic, cycloaliphatic, or aliphatic hydrocarbon group containing from 1 to 28 carbon atoms; and
(ii) an N-aromatically, N-aliphatically, N-cycloaliphatically, or N-araliphatically substituted mono- or oligourethane corresponding to the formula

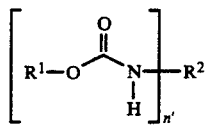

wherein
n' is an integer of from 1 to 6,
$R^1$ is an monofunctional aromatic hydrocarbon group containing 6 to 18 carbon atoms, aliphatic hydrocarbon group containing 1 to 18 carbon atoms, cycloaliphatic hydrocarbon group containing 4 to 30 carbon atoms, or araliphatic hydrocarbon group containing 7 to 30 carbon atoms, and
$R^2$ is an n'-functional aromatic, araliphatic, cycloaliphatic, or aliphatic hydrocarbon group containing from 1 to 28 carbon atoms.

3. A process according to claim 1 wherein component
(a) is an oligourethane corresponding to the formula

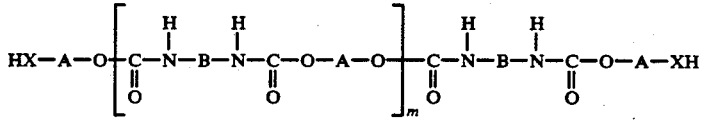

wherein
X is O or NH,
A is a residue of a dihydric alcohol corresponding to a difunctional $R^1$ group,
B is a residue of a diisocyanate corresponding to a difunctional $R^2$ group, and
m is a number of from 1 to 20.

4. A process according to claim 1 wherein the dialkyl carbonate is a compound corresponding to the formula

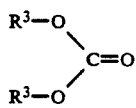

wherein $R^3$ is an aliphatic or araliphatic hydrocarbon group containing 1 to 18 carbon atoms.

5. A process according to claim 1 wherein the dialkyl carbonate is dimethyl carbonate.

6. A process according to claim 1 wherein the alkali carbonate is potassium carbonate, sodium carbonate, or a mixture thereof.

7. A process according to claim 1 wherein the alkali carbonate is dry powdered potassium carbonate.

8. A process according to claim 1 wherein the reaction is carried out in excess dialkyl carbonate.

9. A process according to claim 1 wherein the reaction is carried out in an aprotic organic solvent.

10. A process according to claim 9 wherein the organic solvent is dimethyl sulfoxide, dimethylformamide, N-methylpyrrolidone, or tetramethylene sulfone.

11. A process according to claim 1 wherein the phase transfer catalyst is a tetraalkylammonium chloride, bromide, or iodide.

12. A process for preparing a N,N-disubstituted mono- or oligourethane comprising reacting
  (a) an N-aromatically, N-aliphatically, N-cycloaliphatically, or N-araliphatically substituted mono- or oligourethane
  (b) with dimethyl carbonate in the presence of
  (c) at least stoichiometrically equivalent quantities of dry powdered potassium carbonate in excess dimethyl carbonate or in dimethyl sulfoxide, dimethylformamide, N-methylpyrrolidone, or tetramethylene sulfone and in the presence of a tetraalkylammonium chloride, bromide, or iodide.

* * * * *